US012677833B2

(12) United States Patent
Ju et al.

(10) Patent No.: US 12,677,833 B2
(45) Date of Patent: Jul. 14, 2026

(54) NATURAL EFFICIENT SELF-ASSEMBLED PHOTOTHERMAL ANTIBACTERIAL NANOPARTICLE, PREPARATION METHOD THEREFOR AND USE THEREOF

(71) Applicant: Qingdao Agricultural University, Qingdao (CN)

(72) Inventors: Jian Ju, Qingdao (CN); Fangyuan Zhao, Qingdao (CN); Qingli Yang, Qingdao (CN); Guangjie Che, Qingdao (CN)

(73) Assignee: Qingdao Agricultural University, Qingdao (CN)

( * ) Notice: Subject to any disclaimer, the term of this patent is extended or adjusted under 35 U.S.C. 154(b) by 412 days.

(21) Appl. No.: 18/206,105

(22) Filed: Jun. 6, 2023

(65) Prior Publication Data

US 2024/0268389 A1 Aug. 15, 2024

(30) Foreign Application Priority Data

Feb. 14, 2023 (CN) .......................... 202310114832.5

(51) Int. Cl.
| | |
|---|---|
| *A01N 43/90* | (2006.01) |
| *A01N 25/04* | (2006.01) |
| *B82Y 5/00* | (2011.01) |
| *B82Y 30/00* | (2011.01) |

(52) U.S. Cl.
CPC ............. *A01N 43/90* (2013.01); *A01N 25/04* (2013.01); *B82Y 5/00* (2013.01); *B82Y 30/00* (2013.01)

(58) Field of Classification Search
CPC .......... A01N 43/90; A01N 25/04; B82Y 5/00; B82Y 30/00
See application file for complete search history.

(56) References Cited

PUBLICATIONS

R. Shen, et al. "Carrier-free Chinese herbal small molecules self-assembly with 3D-porous crystal framework as a synergistic anti-AD agent," International Journal of Pharmaceutics 630 (2023) 122458. Available online Nov. 30, 2022. (Year: 2022).*
R. Pei, et al. Rhein Derivatives, A Promising Pivot?, Mini-Reviews in Medicinal Chemistry, 2021, 21, 554-575. (Year: 2021).*
R. Marinho, et al. "Effect of Stirring Speed on Conversion and Time to Particle Stabilization of Poly (Vinyl Chloride) produced by suspension polymerization process at the beginning of reaction," Brazilian Journal of Chemical Engineering, vol. 35, No. 02, pp. 631-640, Apr.-Jun. 2018. (Year: 2018).*
F. Vargas, et al. "Studies on the photostability and phototoxicity of aloe-emodin, emodin and rhein," Die Pharmazie Jun. 2002; 57(6): 399-404. (Year: 2002).*
S. Wu, et al. "A New Perspective on the Antimicrobial Mechanism of Berberine Hydrochloride Against *Staphylococcus aureus* Revealed by Untargeted Metabolomic Studies," Front. Microbiol., Jul. 12, 2022, vol. 13, 2022, 1-13. (Year: 2022).*
Chromium dichloride ($CrCl_2$). PubChem Compound Summary. National Center for Biotechnology Information (NCBI), U.S. National Library of Medicine. Created Mar. 26, 2005, Modified Sep. 27, 2025, pp. 1-57, retrieved from: https://pubchem.ncbi.nlm.nih.gov/compound/Chromium-dichloride.

* cited by examiner

*Primary Examiner* — Michael P Cohen
(74) *Attorney, Agent, or Firm* — Bayramoglu Law Offices LLC

(57) ABSTRACT

A preparation process of the natural efficient self-assembled photothermal antibacterial nanoparticle is provided that includes mixing a solution of berberine in methanol and a solution of rhein of methanol to obtain a mixed solution, and then mixing the mixed solution with water and performing self-assembly reaction to obtain a self-assembled nanoparticle solution; and mixing the self-assembled nanoparticle solution with a solution of chromium chloride in methanol, and performing coordination reaction to obtain the natural efficient self-assembled photothermal antibacterial nanoparticle. The natural efficient self-assembled photothermal antibacterial nanoparticle prepared by the present invention can quickly raise the temperature under irradiation of near-infrared long-wave light, thus playing a role in instantaneous broad-spectrum sterilization. Because the berberine and the rhein have antibacterial effects, the prepared nanoparticle has a double synergistic sterilization effect under the irradiation of near-infrared long-wave light.

7 Claims, 3 Drawing Sheets

NATURAL EFFICIENT SELF-ASSEMBLED PHOTOTHERMAL ANTIBACTERIAL NANOPARTICLE, PREPARATION METHOD THEREFOR AND USE THEREOF

CROSS REFERENCE TO RELATED APPLICATIONS

This application is based upon and claims priority to Chinese Application No. 202310114832.5 filed Feb. 14, 2023, the entire contents of which are incorporated by reference herein.

TECHNICAL FIELD

The present invention relates to the technical field of food sterilization, and in particular to a natural efficient self-assembled photothermal antibacterial nanoparticle, a preparation method therefor, and use thereof.

BACKGROUND

Various industrial materials, medical biomaterials, sanitary products, agricultural products or food are easy to contact and hide a large amount of bacteria during processing process, which seriously threatens human health. Antibiotics are still currently considered to be a main strategy for treatment of bacterial infections. However, long-term overuse of antibiotics can lead to accelerated evolution and emergence of antibiotic-resistant bacteria. At the same time, the variety of new antibiotics on the market is gradually decreasing. Therefore, relying solely on antibiotics to control bacterial infections further increases a risk of bacterial resistance.

Currently, development of natural antibacterial agents is receiving more and more attention, however, the problem of low antibacterial activity of natural antibacterial agents in practical application is common. The photodynamic sterilization can inactivate microorganisms by using local heat generated by light irradiation, is an effective physical sterilization method, and cannot cause the generation of microbial resistance. Therefore, further improving sterilization activity of natural antibacterial agents by means of photodynamic sterilization technology is a potential solution. Some metal (such as Au, Ag, and Cu) nanoparticles are currently used as photothermal sterilization materials due to their good photothermal conversion efficiency. Unfortunately, these metal nanoparticles usually have certain cytotoxicity and are not easily degraded, and long-term use may pose a threat to human health and the environment, and further popularization and application thereof are severely restricted.

Therefore, development of a natural, efficient and biocompatible photothermal bactericide has very important practical application value.

SUMMARY

An objective of the present invention is to provide a natural efficient self-assembled photothermal antibacterial nanoparticle, a preparation method therefor, and use thereof, so as to solve the problem in the prior art.

In order to achieve the above objective, the present invention provides the following technical solutions.

The present invention provides a preparation method for a natural efficient self-assembled photothermal antibacterial nanoparticle, which comprises the following steps:

(1) mixing a solution of berberine in methanol and a solution of rhein of methanol to obtain a mixed solution, and then mixing the mixed solution with water and performing self-assembly reaction to obtain a self-assembled nanoparticle solution;

(2) mixing the self-assembled nanoparticle solution with a solution of chromium chloride in methanol, and performing coordination reaction to obtain the natural efficient self-assembled photothermal antibacterial nanoparticle.

Preferably, in the preparation method for the natural efficient self-assembled photothermal antibacterial nanoparticle, the solution of berberine in methanol in the step (1) has a concentration of 3-5 wt %, and the solution of rhein in methanol in the step (1) has a concentration of 2-4 wt %.

Preferably, in the preparation method for the natural efficient self-assembled photothermal antibacterial nanoparticle, a volume ratio of the solution of berberine in methanol and the solution of rhein in methanol in the step (1) is 1-3:1-3, and a volume ratio of the mixed solution and water in the step (1) and the solution of chromium chloride in methanol in the step (2) is 8-10:80-100:10-12.

Preferably, in the preparation method for the natural efficient self-assembled photothermal antibacterial nanoparticle, the self-assembly reaction in the step (1) is performed for 5-6 h, the self-assembly reaction is performed at a temperature of 60-70° C., and stirring is performed at a rotation speed of 300-600 r/min.

Preferably, in the preparation method for the natural efficient self-assembled photothermal antibacterial nanoparticle, a molar volume ratio of the chromium chloride in the solution of chromium chloride in methanol to the solution of chromium chloride in methanol in the step (2) is 0.5-1 mmol:5-15 mL.

Preferably, in the preparation method for the natural efficient self-assembled photothermal antibacterial nanoparticle, the coordination reaction in the step (2) is performed in the dark, the coordination reaction is performed at a temperature of 20-25° C., and the coordination reaction is performed for 4-6 h.

Preferably, in the preparation method for the natural efficient self-assembled photothermal antibacterial nanoparticle, the step (2) further comprises: after the coordination reaction is completed, dialyzing, wherein the dialysis is performed at a temperature of 2-10° C., and the dialysis is performed for 24-36 h.

The present invention further provides a natural efficient self-assembled photothermal antibacterial nanoparticle prepared by the preparation method for the natural efficient self-assembled photothermal antibacterial nanoparticle.

The present invention further provides use of the natural efficient self-assembled photothermal antibacterial nanoparticle in the preparation of an antibacterial agent.

It can be known from the technical solutions that, compared with the prior art, the present invention has the following beneficial effects.

(1) The berberine and rhein are self-assembled to prepare a nanoparticle, and then reacted with chromium chloride to obtain a natural nanoparticle with a particle size of 50-140 nm. The nanoparticle significantly improves physicochemical stability and the bioavailability of the berberine and the rhein in practical application.

(2) The nanoparticle prepared by the present invention can quickly raise the temperature under the irradiation of near-infrared long-wave light (NILWL), thereby achieving the effect of instantaneous broad-spectrum sterilization. The berberine and the rhein have antibacterial effects, that is, the prepared nanoparticle can realize double synergistic sterilization effects under the irradiation of NILWL, and has high sterilization activity on drug-resistant strains.

(3) The natural efficient self-assembled photothermal antibacterial nanoparticle prepared by the present invention has the characteristics of good biocompatibility, greenness, safety and no toxicity.

(4) The preparation method of the present invention is simple and convenient, is easy to operate, does not generate any toxic and harmful byproducts and the like, and is suitable for large-scale production and application.

BRIEF DESCRIPTION OF THE DRAWINGS

In order to more clearly illustrate the technical solutions in the examples of the present invention or in the prior art, the drawings used in the description of the examples or the prior art are briefly introduced below.

DETAILED DESCRIPTION OF THE EMBODIMENTS

Figure 1:
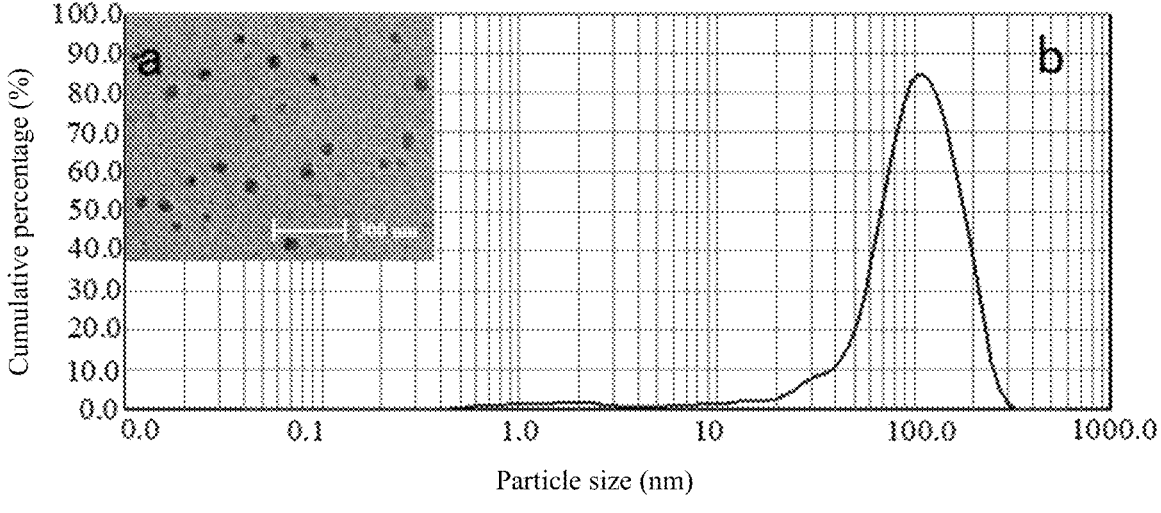
FIG. 1 is a particle size distribution diagram and a transmission electron microscope of a natural efficient self-assembled photothermal antibacterial nanoparticle in Example 1; where a is a particle size distribution diagram, and b is a transmission electron microscope image.

The present invention provides a preparation method for a natural efficient self-assembled photothermal antibacterial nanoparticle, which comprises the following steps:

(1) mixing a solution of berberine in methanol and a solution of rhein of methanol to obtain a mixed solution, and then mixing the mixed solution with water and performing self-assembly reaction to obtain a self-assembled nanoparticle solution;

(2) mixing the self-assembled nanoparticle solution with a solution of chromium chloride in methanol, and performing coordination reaction to obtain the natural efficient self-assembled photothermal antibacterial nanoparticle.

In the present invention, mixing the solution of berberine in methanol and the solution of rhein in methanol in the step (1) is performed at a temperature of preferably 25-30° C., further preferably 25, 26, 27, 28, 29 or 30° C., and more preferably 28° C.; and the mixing method is stirring, the stirring is performed for preferably 30-60 min, further preferably 30, 35, 40, 45, 50, 55 or 60 min, and more preferably 50 min, and the stirring is performed at a rotation speed of preferably 1000 r/min.

In the present invention, the solution of berberine in methanol in the step (1) has a concentration of preferably 3-5 wt %, further preferably 3, 3.2, 3.5, 4, 4.5, 4.7 or 5 wt %, and more preferably 4 wt %; and the solution of rhein in methanol in the step (1) has a concentration of preferably 2-4 wt %, further preferably 2, 2.3, 2.5, 2.8, 3, 3.5, 3.8 or 4 wt %, and more preferably 3 or 3.5 wt %.

In the present invention, the volume ratio of the solution of berberine in methanol and the solution of rhein in methanol in the step (1) is preferably 1-3:1-3, further preferably 1.2-2.7:1.2-2.7, and more preferably 1.5:2; and the volume ratio of the mixed solution and water in the step (1) and the solution of chromium chloride in methanol in the step (2) is preferably 8-10:80-100:10-12, further preferably 8.2-9.7:82-97:10.5-11.8, and more preferably 8.5:85:11.

In the present invention, the self-assembly reaction in the step (1) is performed for preferably 5-6 h, further preferably 5, 5.25, 5.5, 5.75 or 6 h, and more preferably 5.5 h; the self-assembly reaction is performed at a temperature of preferably 60-70° C., further preferably 60, 62, 65, 68 or 70° C., and more preferably 60° C.; and the stirring is performed at a rotation speed of preferably 400-600 r/min, further preferably 400, 450, 500, 550 or 600 r/min, and more preferably 450 r/min.

In the present invention, the molar volume ratio of the chromium chloride in the solution of chromium chloride in methanol to the solution of chromium chloride in methanol in the step (2) is 0.5-1 mmol:5-15 mL, further preferably 0.65-0.85 mmol:7-13 mL, and more preferably 0.7 mmol:9 mL.

In the present invention, a specific method for mixing in the step (2) is stirring, the stirring is performed for preferably 5-10 min, further preferably 5, 6, 7, 8, 9 or 10 min, and more preferably 7 or 8 min, and the stirring is performed at a rotation speed of preferably 400-600 r/min, further preferably 400, 450, 500, 550 or 600 r/min, and more preferably 450 r/min.

In the present invention, the coordination reaction in the step (2) is performed by stirring in the dark, the coordination reaction is performed at a temperature of preferably 20-25° C., further preferably 20, 21, 22, 23, 24 or 25° C., and more preferably 20° C.; the coordination reaction is performed for preferably 4-6 h, further preferably 4, 4.25, 4.75, 5, 5.5, 5.75 or 6 h, and more preferably 5 h; and the stirring is performed at a rotation speed of preferably 400 r/min.

In the present invention, the step (2) further comprises: after the coordination reaction is completed, dialyzing, wherein the dialysis is performed at a temperature of preferably 2-10° C., further preferably 2, 4, 5, 6, 8 or 10° C., and more preferably 4 or 5° C.; and the dialysis is performed for preferably 24-36 h, further preferably 24, 25, 28, 30, 32, 35 or 36 h, and more preferably 30 h.

The present invention further provides a natural efficient self-assembled photothermal antibacterial nanoparticle prepared by the preparation method for the natural efficient self-assembled photothermal antibacterial nanoparticle.

The present invention further provides use of the natural efficient self-assembled photothermal antibacterial nanoparticle in the preparation of an antibacterial agent.

The technical solutions in the examples of the present invention will be clearly and completely described below. Apparently, the described examples are merely illustrative, rather than limiting on the present invention. Based on the examples of the present invention, all other examples obtained by those of ordinary skilled in the art without creative efforts are intended to fall within the protection scope of the present patent.

Example 1

(1) 3 wt % of a solution of berberine in methanol with a pH value of 7 and 2 wt % of a solution of rhein in methanol with a pH value of 7 were prepared;

3 wt % of the solution of berberine in methanol and 2 wt % of the solution of rhein in methanol were mixed in a volume ratio of 1:1 at a rotation speed of 1000 r/min for 30 min at a temperature of 25° C. to obtain a mixed solution, then 8 mL of the mixed solution was taken and mixed with 80 mL of distilled water at a temperature of 60° C. with the temperature maintained at 60° C., stirred at the rotation speed of 450 r/min, and subjected to self-assembly reaction for 5 h to obtain a self-assembled nanoparticle solution;

(2) the self-assembled nanoparticle solution and 10 mL of the solution of chromium chloride in methanol (the content of chromium chloride was 0.5 mmol) were stirred at a rotation speed of 450 r/min and stirred for 5 min, then stirred at a rotation speed of 400 r/min in the dark at the room temperature, and subjected to coordination reaction for 4 h; and the mixture was dialyzed with deionized water at 4° C. for 24 h after the coordination reaction was completed to obtain a natural efficient self-assembled photothermal antibacterial nanoparticle.

The particle size distribution diagram and transmission electron microscope (TEM) image of the above prepared natural efficient self-assembled photothermal antibacterial nanoparticle are shown in FIG. 1. As shown in FIG. 1, most of the natural efficient self-assembled photothermal antibacterial nanoparticle were approximately uniform spherical particles with a size of about 50-140 nm.

Example 2

(1) 4 wt % of a solution of berberine in methanol with a pH value of 7 and 3 wt % of a solution of rhein in methanol with a pH value of 7 were prepared;

4 wt % of the solution of berberine in methanol and 3 wt % of the solution of rhein in methanol were mixed in a volume ratio of 2:1 at a rotation speed of 1000 r/min for 45 min at a temperature of 28° C. to obtain a mixed solution, then 9 mL of the mixed solution was taken and mixed with 90 mL of distilled water at a temperature of 65° C. with the temperature maintained at 65° C., stirred at the rotation speed of 450 r/min, and subjected to self-assembly reaction for 5.5 h to obtain a self-assembled nanoparticle solution;

(2) the self-assembled nanoparticle solution and 10 mL of the solution of chromium chloride in methanol (the content of chromium chloride was 0.8 mmol) were stirred at a rotation speed of 450 r/min and stirred for 5 min, then stirred at a rotation speed of 400 r/min in the dark at the room temperature, and subjected to coordination reaction for 5 h; and the mixture was dialyzed with deionized water at 4° C.

for 30 h after the coordination reaction was completed to obtain a natural efficient self-assembled photothermal antibacterial nanoparticle.

Example 3

(1) 5 wt % of a solution of berberine in methanol with a pH value of 7 and 4 wt % of a solution of rhein in methanol with a pH value of 7 were prepared;

5 wt % of the solution of berberine in methanol and 4 wt % of the solution of rhein in methanol were mixed in a volume ratio of 1.5:2 at a rotation speed of 1000 r/min for 60 min at a temperature of 30° C. to obtain a mixed solution, then 10 mL of the mixed solution was taken and mixed with 100 mL of distilled water at a temperature of 70° C. with the temperature maintained at 70° C., stirred at the rotation speed of 450 r/min, and subjected to self-assembly reaction for 6 h to obtain a self-assembled nanoparticle solution;

(2) the self-assembled nanoparticle solution and 10 mL of the solution of chromium chloride in methanol (the content of chromium chloride was 1.0 mmol) were stirred at a rotation speed of 450 r/min and stirred for 5 min, then stirred at a rotation speed of 400 r/min in the dark at the room temperature, and subjected to coordination reaction for 6 h; and the mixture was dialyzed with deionized water at 4° C. for 36 h after the coordination reaction was completed to obtain a natural efficient self-assembled photothermal antibacterial nanoparticle.

Comparative Example 1

4 wt % of a solution of berberine in methanol with a pH value of 7 and 3 wt % of a solution of rhein in methanol with a pH value of 7 were prepared; 4 wt % of the solution of berberine in methanol and 3 wt % of the solution of rhein in methanol were mixed in a volume ratio of 2:1 at a rotation speed of 1000 r/min for 45 min at a temperature of 28° C. to obtain a mixed solution, then 9 mL of the mixed solution was taken and mixed with 90 mL of distilled water at a temperature of 65° C. with the temperature maintained at 65° C., stirred at the rotation speed of 450 r/min, and subjected to self-assembly reaction for 5.5 h to obtain a natural self-assembled antimicrobial nanoparticle solution.

Figure 2:
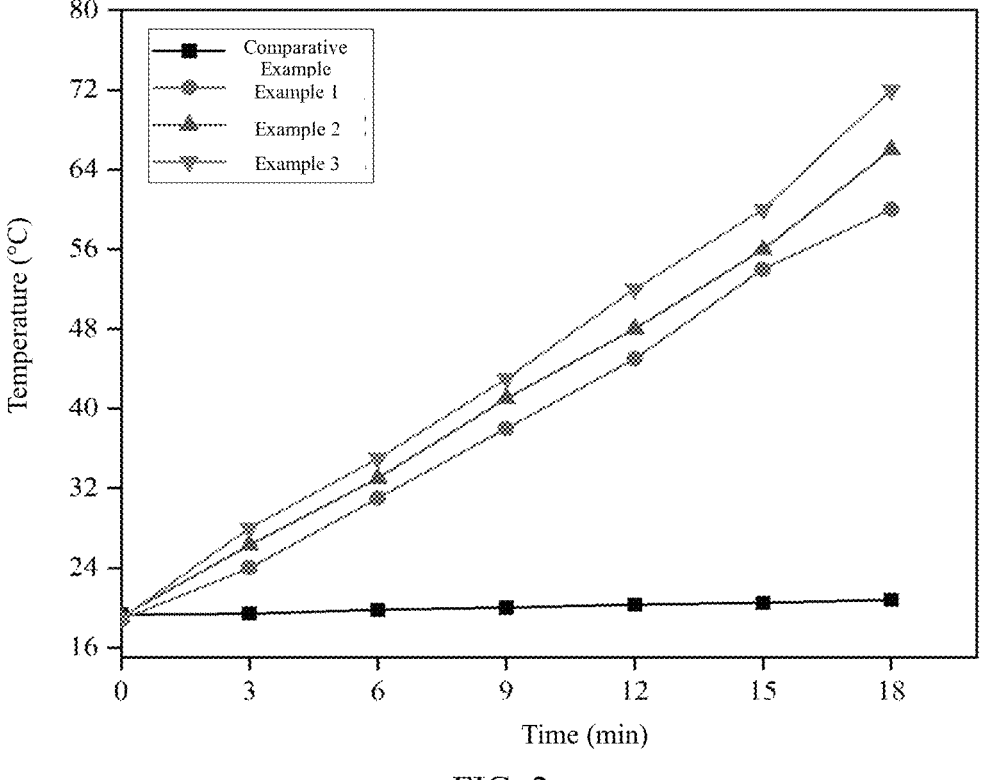
FIG. 2 is a photothermal performance diagram of a natural efficient self-assembled photothermal antibacterial nanoparticle in Examples 1 to 3 and a natural self-assembled antibacterial nanoparticle in a comparative example.

Photothermal Measurement:

The natural efficient self-assembled photothermal antibacterial nanoparticle in Examples 1 to 3 and the natural self-assembled antibacterial nanoparticle in Comparative Example 1 were prepared into nanoparticle solutions with a concentration of 5 mg/mL with distilled water, 300 μL of the solutions were added into a 3 mL centrifuge tube, and the temperature changes were measured with an SH-X temperature tester after irradiation with near-infrared long-wave light (NILWL) (wavelength: 1500 nm, power: 2 W/cm$^2$) for 0 min, 3 min, 6 min, 9 min, 12 min, 15 min, and 18 min, and the results were shown in FIG. 2.

It can be seen from FIG. 2 that the nanoparticle in Comparative Example 1, to which no chromium chloride was added, had no significant increase in temperature after irradiation with near-infrared long-wave light (NILWL). However, the temperature of the nanoparticle in Examples 1 to 3 was significantly increased, which indicated that the simple self-assembled nanoparticle of berberine and rhein cannot generate heat energy under the NILWL irradiation, the photothermal property of the nanoparticle in Examples 1 to 3 was provided by the chromium ions wrapped on an outer surface of the particle, and the temperature of the nanoparticle in Example 3 was increased most rapidly after the NILWL irradiation, which indicated that the photothermal performance of the nanoparticle was in direct proportion to the addition amount of chromium chloride in a certain range.

Sterilization Performance Determination:

(1) Determination of Sterilization Performance on Methicillin-Resistant *Staphylococcus aureus* (MRSA):

a light group: methicillin-resistant *Staphylococcus aureus* cultured to the logarithmic phase was taken and prepared into bacterial suspension having a concentration of 105 CFU/mL by using sterile distilled water, the natural efficient self-assembled photothermal antibacterial nanoparticle in Example 1 was prepared into a nanoparticle solution with a concentration of 5 mg/mL by using distilled water, 100 μL of the bacterial suspension and 100 μL of the nanoparticle solution were mixed to obtain a sample, and the sample was irradiated for 9 min under NILWL; then, a plate colony counting method was used to determine the sterilization activity of the sample, and the specific method comprised the following steps: taking 100 μL of sample, coating the sample on a nutrient agar plate, culturing for 24 h at 37° C., counting colonies, repeating for three times, and taking an average value;

a control group without light: the conditions were consistent with those of the light group, the only difference was that the sample was placed in the dark environment for 9 min;

a blank control group with light: the conditions were consistent with those of the light group, the only difference was that the natural efficient self-assembled photothermal antibacterial nanoparticle solution was replaced with the sterile distilled water;

a blank control group without light: the conditions were consistent with those of the control group without light, the only difference was that the natural efficient self-assembled photothermal antibacterial nanoparticle solution was replaced with the sterile distilled water.

(2) Determination of Sterilization Performance on *Escherichia coli* (*E. coli*):

This determination method was consistent with the determination method of sterilization performance of the natural self-assembled antimicrobial nanoparticle solution on methicillin-resistant *Staphylococcus aureus* (MRSA), the only difference was that the methicillin-resistant *Staphylococcus aureus* was replaced with *Escherichia coli*.

The natural efficient self-assembled photothermal antibacterial nanoparticle in Examples 2 to 3 and the natural self-assembled antibacterial nanoparticle in Comparative Example 1 were subjected to the same method to test the sterilization performance on methicillin-resistant *Staphylococcus aureus* and *Escherichia coli*.

Figures 3, 4:
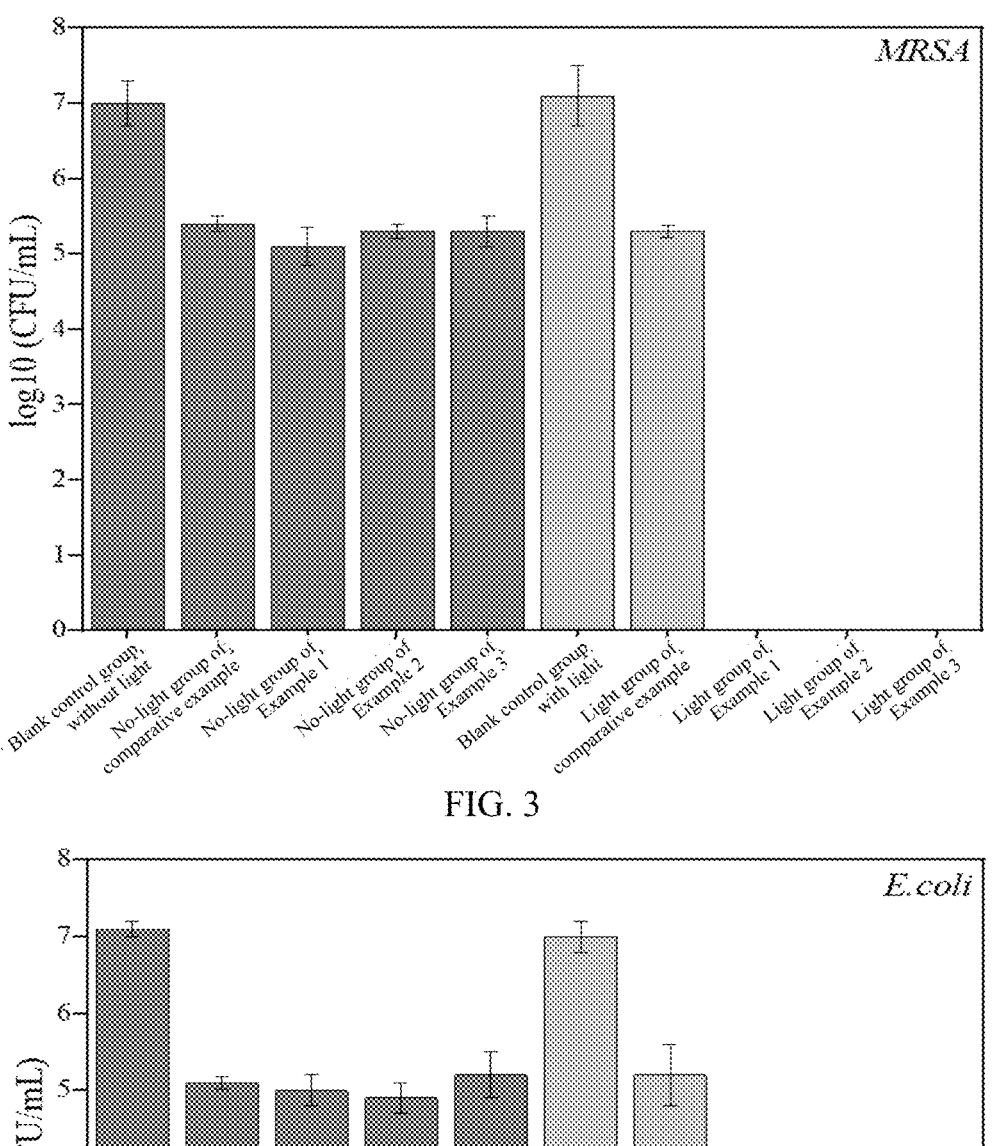
FIG. 3 is a graph showing a sterilization performance of a natural efficient self-assembled photothermal antibacterial nanoparticle in Examples 1 to 3 and a natural self-assembled antibacterial nanoparticle in a comparative example on methicillin-resistant *Staphylococcus aureus*.
FIG. 4 is a graph showing a sterilization performance of a natural efficient self-assembled photothermal antibacterial nanoparticle in Examples 1 to 3 and a natural self-assembled antibacterial nanoparticle in a comparative example on *Escherichia coli*.

The sterilization effect of the natural efficient self-assembled photothermal antibacterial nanoparticle in Examples 1 to 3 and the natural self-assembled antibacterial nanoparticle in Comparative Example 1 on MRSA is shown in FIG. 3, and the sterilization effect of the natural efficient self-assembled photothermal antibacterial nanoparticle in Examples 1 to 3 and the natural self-assembled antibacterial nanoparticle in Comparative Example 1 on *E. coli* is shown in FIG. 4.

It can be seen from FIGS. 3 and 4, the numbers of colonies in the no-light group of Comparative Example 1 and the light group of Comparative Example 1 were not significantly different, whereas the numbers of colonies in the no-light group of Comparative Example 1 and the light group of Comparative Example 1 were significantly reduced compared to those of the blank control group without light and blank control group with light, which mainly resulted from the antibacterial activity of berberine and rhein in Comparative Example 1. It is worth mentioning that, it can be clearly seen from FIGS. 3 and 4, the total number of colonies in all the light groups of examples was significantly decreased as compared with that of the no-light groups of examples, and MRSA and *E. coli* were not detected in all the light groups of Examples 1 to 3. This fully indicated that the natural efficient self-assembled photothermal antibacterial nanoparticle prepared in Examples 1 to 3 showed efficient sterilization activity on bacteria including drug-resistant bacteria. At the same time, this indicated that the NILWL irradiation treatment can significantly enhance the antibacterial activity of the nanoparticles. The photothermal effect of the self-assembled antibacterial nanoparticle and the antibacterial activity of the berberine and the rhein realized the synergistic efficient sterilization.

Assay of Application in Food Models:

a light group: the natural efficient self-assembled photothermal antibacterial nanoparticle in Example 1 was prepared into a nanoparticle solution with a concentration of 5 mg/mL by using distilled water, 10 μL of the prepared MRSA bacterial suspension (with a concentration of 105 CFU/mL) was uniformly mixed with an equal volume of the nanoparticle solution to obtain a sample, the sample was irradiated by NILWL for 9 min and then coated on a surface of fresh pork with a size of 3 cm×2 cm×2 cm, the pork was placed at 37° C. for 6 h, and then the bacterial viability was determined by a plate colony counting method, wherein the bacterial viability (%) was obtained by dividing the number of colonies of the experimental sample by the number of colonies of the blank control sample and then multiplying by 100%, and each sample was in triplicate and averaged.

A control group without light: the conditions were consistent with those of the light group, the only difference was that the sample was placed in the dark environment for 9 min;

a blank control group: the conditions were consistent with those of the light group, the only difference was that the natural efficient self-assembled photothermal antibacterial nanoparticle solution was replaced with the sterile distilled water;

the same method was used to determine the sterilization effect of each group of samples on *E. coli* in the food models. Meanwhile, the natural efficient self-assembled photothermal antibacterial nanoparticle in Examples 2 to 3 and the natural self-assembled antibacterial nanoparticle in Comparative Example 1 were tested by the same method.

Figure 5:
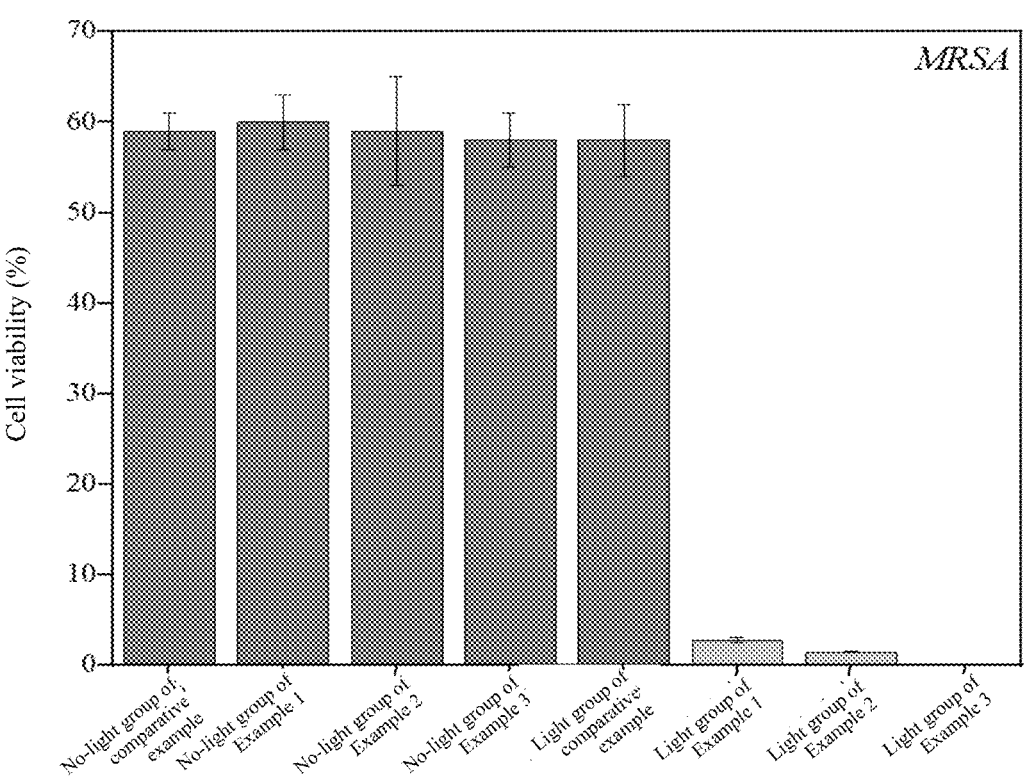
FIG. 5 is a graph showing a sterilization performance of a natural efficient self-assembled photothermal antibacterial nanoparticle in Examples 1 to 3 and a natural self-assembled antibacterial nanoparticle in a comparative example on methicillin-resistant *Staphylococcus aureus* in a food model.
Figure 6:
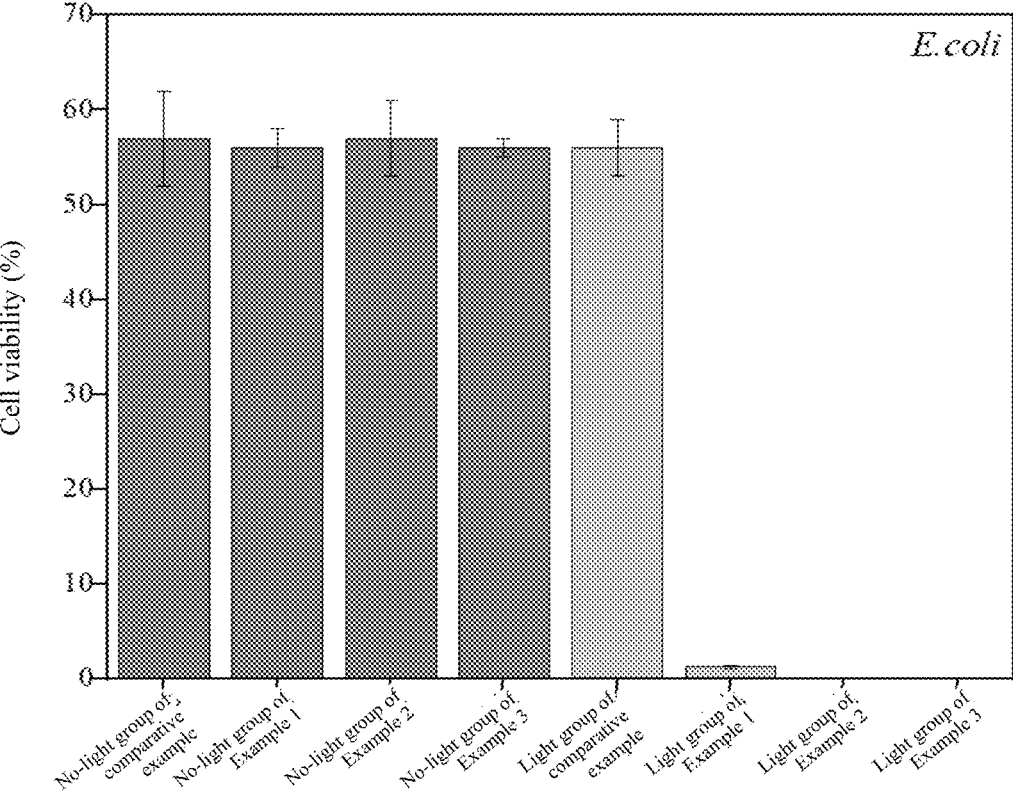
FIG. 6 is a graph showing a sterilization performance of a natural efficient self-assembled photothermal antibacterial nanoparticle in Examples 1 to 3 and a natural self-assembled antimicrobial nanoparticle in a comparative example on *Escherichia coli* in a food model.

The sterilization effect of the natural efficient self-assembled photothermal antibacterial nanoparticle in Examples 1 to 3 and the natural self-assembled antibacterial nanoparticle in Comparative Example 1 on MRSA in the food models is shown in FIG. 5, and the sterilization effect of natural efficient self-assembled photothermal antibacterial nanoparticle in Examples 1 to 3 and the natural self-assembled antibacterial nanoparticle in Comparative Example 1 on *E. coli* in the food models is shown in FIG. 6.

It can be seen from FIGS. 5 and 6, the viabilities of MRSA and *E. coli* in the pork treated by the nanoparticle of the light and no-light groups of Comparative Example 1 and the no-light groups of Examples 1 to 3 were both 55% or more, which indicated that the nanoparticle of the light and no-light groups of Comparative Example 1 and the no-light groups of Examples 1 to 3 had a certain sterilization activity, however, the sterilization effect was not ideal. As described above, the reason why a certain sterilization activity was shown was due to the sterilization activity possessed by berberine and rhein themselves. However, it can be clearly seen from the figures that the viabilities of MRSA and *E. coli* in the NILWL irradiation treatment groups of Examples 1 to 3 were significantly decreased, where the viabilities for MRSA were decreased to 2.8%, 1.5%, and 0%, and the viabilities for *E. coli* were decreased to 1.3%, 0%, and 0%. This indicated that the natural efficient self-assembled photothermal antibacterial nanoparticle prepared by the present invention still has efficient sterilization activity even in the practical application of food models, so that the natural efficient self-assembled photothermal antibacterial nanoparticle has great practical application value as a natural green efficient bactericide.

The above descriptions are only preferred examples of the present invention. It should be noted that those of ordinary skill in the art can also make several improvements and modifications without departing from the principle of the present invention, and such improvements and modifications shall fall within the protection scope of the present invention.

What is claimed is:

1. A preparation method for a natural efficient self-assembled photothermal antibacterial nanoparticle, comprising the following steps:

(1) mixing a solution of berberine in methanol and a solution of rhein of methanol to obtain a mixed solution, and then mixing the mixed solution with water and performing self-assembly reaction to obtain a self-assembled nanoparticle solution;

(2) mixing the self-assembled nanoparticle solution with a solution of chromium chloride in methanol, and performing coordination reaction to obtain the natural efficient self-assembled photothermal antibacterial nanoparticle;

wherein a volume ratio of the solution of berberine in methanol and the solution of rhein in methanol in the step (1) is 1-3:1-3, and a volume ratio of the mixed solution and water in the step (1) and the solution of chromium chloride in methanol in the step (2) is 8-10:80-100:10-12;

wherein the self-assembly reaction in the step (1) is performed for 5-6 h, the self-assembly reaction is performed at a temperature of 60-70° C., and stirring is performed at a rotation speed of 300-600 r/min; and wherein a molar volume ratio of the chromium chloride in the solution of chromium chloride in methanol to the solution of chromium chloride in methanol in the step (2) is 0.5-1 mmol:5-15 mL.

2. The preparation method for the natural efficient self-assembled photothermal antibacterial nanoparticle according to claim 1, wherein the solution of berberine in methanol in the step (1) has a concentration of 3-5 wt %, and the solution of rhein in methanol in the step (1) has a concentration of 2-4 wt %.

3. A natural efficient self-assembled photothermal antibacterial nanoparticle prepared by the preparation method for the natural efficient self-assembled photothermal antibacterial nanoparticle according to claim 2.

4. The preparation method for the natural efficient self-assembled photothermal antibacterial nanoparticle according to claim 1, wherein the coordination reaction in the step (2) is performed in the dark, the coordination reaction is performed at a temperature of 20-25° C., and the coordination reaction is performed for 4-6 h.

5. The preparation method for the natural efficient self-assembled photothermal antibacterial nanoparticle according to claim 1, wherein the step (2) further comprises: after the coordination reaction is completed, dialyzing, wherein the dialysis is performed at a temperature of 2-10° C., and the dialysis is performed for 24-36 h.

6. A natural efficient self-assembled photothermal antibacterial nanoparticle prepared by the preparation method for the natural efficient self-assembled photothermal antibacterial nanoparticle according to claim 1.

7. A method of using the natural efficient self-assembled photothermal antibacterial nanoparticle according to claim 6 in the preparation of an antibacterial agent, comprising a step of contacting a bacteria with the natural efficient self-assembled photothermal antibacterial nanoparticle.

* * * * *